United States Patent
Brand

(10) Patent No.: US 6,628,979 B2
(45) Date of Patent: Sep. 30, 2003

(54) METHOD AND DEVICE FOR INCREASING THE EFFICIENCY OF A GRADIENT SYSTEM IN A MAGNETIC RESONANCE TOMOGRAPHY APPARATUS

(75) Inventor: Martin Brand, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 219 days.

(21) Appl. No.: 09/799,249

(22) Filed: Mar. 5, 2001

(65) Prior Publication Data

US 2001/0020120 A1 Sep. 6, 2001

(30) Foreign Application Priority Data

Mar. 6, 2000 (DE) .......................... 100 10 899

(51) Int. Cl.[7] .................................. A61B 5/05
(52) U.S. Cl. ...................... 600/411; 600/410; 600/546; 324/318
(58) Field of Search ................. 600/411, 410, 600/421, 546, 547, 554; 607/63; 324/306, 307, 318, 322

(56) References Cited

U.S. PATENT DOCUMENTS

| 5,020,542 | A | * | 6/1991 | Rossmann et al. ........... 600/554 |
| 5,245,287 | A | | 9/1993 | Nowak et al. |
| 5,497,773 | A | | 3/1996 | Kuhara et al. |
| 5,561,371 | A | * | 10/1996 | Schenck ..................... 324/318 |
| 5,957,860 | A | * | 9/1999 | Rodiera Olive ............ 600/546 |
| 6,169,403 | B1 | | 1/2001 | Hebrank et al. |
| 6,418,336 | B1 | * | 7/2002 | Kimmlingen et al. ....... 600/410 |

OTHER PUBLICATIONS

"Peripheral Nerve Stimulation by Time–Varying Magnetic Fields" (J. Abart, et al; J. Computer Assisted Tomography (1997) 21 (4):532–8).*

* cited by examiner

Primary Examiner—Quang T. Van
(74) Attorney, Agent, or Firm—Schiff Hardin & Waite

(57) ABSTRACT

In a method and device for increasing the efficiency of a gradient coil system in a magnetic resonance tomography apparatus to optimally use the efficiency of the gradient system, the individually different sensitivity of each patient regarding peripheral nerve stimulation (PNS) is determined prior to the MR examination by applying a variable electrical field, and the corresponding maximum magnetic field is determined by scaling, and the MR apparatus is correspondingly adjusted.

13 Claims, 1 Drawing Sheet

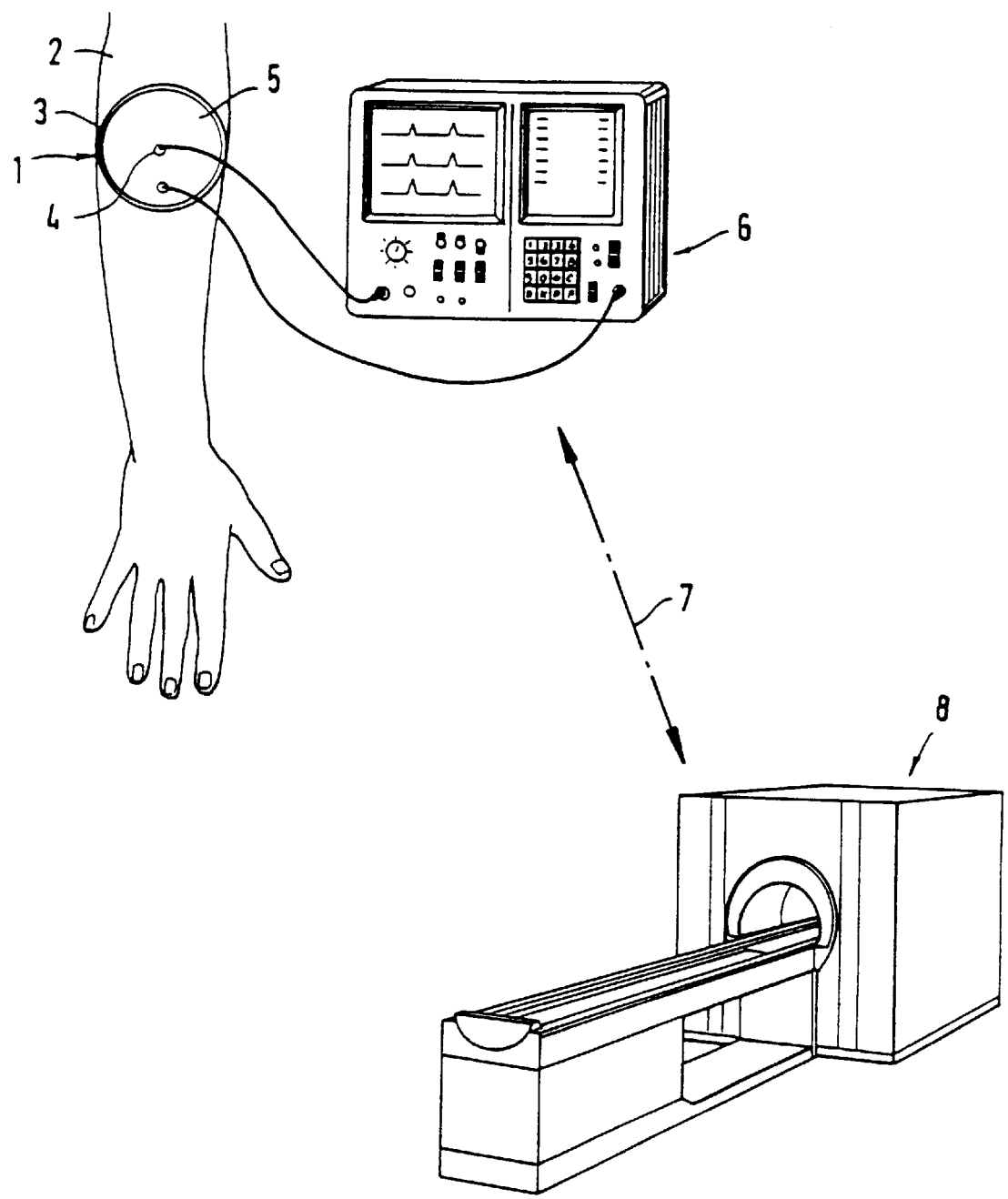

METHOD AND DEVICE FOR INCREASING THE EFFICIENCY OF A GRADIENT SYSTEM IN A MAGNETIC RESONANCE TOMOGRAPHY APPARATUS

BACKGROUND OF THE INVENTION

1. Field of the Invention

The present invention relates to a method for optimally utilizing the efficiency of the gradient system a magnetic resonance of (MR) tomography apparatus and a device for implementing such a method.

2. Description of the Prior Art

Many pulse sequences for imaging with an MR tomography apparatus employ rapidly switched gradient fields. The efficiency of the gradient system cannot be fully utilized, since the rapidly switched magnetic fields, in the upper performance range, cause peripheral nerve stimulations (PNS) in the patient. The stimulation effects are caused by the electrical fields induced by the gradient fields in the body of the patient. The electrical field intensity grows with the amplitude and the frequency of the gradient field. The nervous system of the patient is activated when a physiology-dependent threshold value is exceeded. The patient perceives these stimulations as tingling or twitching in the body.

Clinical tests are currently carried out with new gradient systems, whereby the threshold values of a number of test persons are respectively determined. The limitations regarding the clinical operation of the device are determined from these individual thresholds on the basis of averaging. Although these fixed limitations generally prevent stimulations, a considerable range remains unused with respect to the majority of patients, since the fixed limitation must be set based on the particularly sensitive patient. Peripheral nerve stimulations still occur at individual patients even given this considerable limitation on the actual efficiency of the devices.

This limitation cannot be prevented either by a method for simulating electrical stimulations that are generated by gradient coils, as described in German OS 199 13 547. In such a system, the reference to the individual sensitivity of the individual patient is also missing, so that fixed stimulation values are assumed again, and the gradient field is no longer increased when they are reached.

SUMMARY OF THE INVENTION

An object of the invention is to provide a method and a device that is suitable for its implementation, so that it is possible to enable an optimal adjustment and complete utilization of the efficiency of the gradient system on an individual basis corresponding to the sensitivity of each patient.

This object is achieved in accordance with the invention in method and apparatus wherein the individually different sensitivity of each patient with respect to peripheral nerve stimulations is determined prior to the MR examination by applying a variable electrical field to the patient and wherein a test field is measured, the corresponding maximum magnetic field is determined by scaling from the test field, and the magnetic resonance apparatus is correspondingly adjusted so that the gradient system does not produce a magnetic field higher than the maximum magnetic field.

As a result of the inventive method of an individual, examination preceding determination of the sensitivity of the respective patient, an overall operation below the available efficiency of the devices is not necessary because the maximum magnetic field intensity that can be tolerated by the patient determined before the examination, so that the parameters are correspondingly optimized during the MR tomography sequence. This determination can be carried out while the patient being prepared for the MR examination, so that substantially not decrease in the patient throughput occurs. Moreover, there is no danger for the patient, since the generated test fields are locally extremely limited and the generated stimulations are extremely weak.

The variable electrical field can be generated by electro stimulations with a test electrode attached to the body of the patient. This presents a difficulty, however, is present, since the arising fields are extremely different from the fields induced by magnetic fields. To avoid this difficulty, in a further embodiment of the invention the variable electrical field is generated as an induction field by a test coil that is attached to the body of the patient. The same excitation mechanism is used for this type of prior testing of the sensitivity of the respective patient as for the MR examination, so that test measurements can be better compared with the later impairments as a result of the rapidly switching gradient fields of the MR tomography system. Preferably, the time function of the test field—regardless of whether it is a variable electrical field by means of electro-stimulation or a variable electrical field as induction field of a test coil—has stimulation-relevant characteristics that correspond to the time function of the respective MR gradient field in order to guarantee the same, and therefore closely comparable, conditions.

In addition to starting the electro-stimulation, which can be determined by interrogating the patient during the test, it has proven to be particularly expedient, as a result of the greater objectivity and the simpler applicability of the test results, to detect the peripheral nerve stimulation of the patient by the test field, that is chronologically offset vis-a-vis the excitation, using a measuring electrode. This measuring electrode can be arranged in the center of the test coil. Alternatively the never stimulation can be detected by the test electrode itself.

A device for implementing the inventive method has a measuring amplifier with an adjustable frequency for driving the test electrode or the test coil and for measuring and evaluating the signal of the measuring electrode and a conversion unit for scaling the test field with the MR gradient field.

Preferably, the conversion unit has a memory, in which the field calculation is stored for each gradient orientation and each patient position in order to enable a correlation with the test measurements and the utilized fields. As describe above the inventive arrangement and the inventive method allow the individual sensitivity of the patient to be measured prior to the MR examination and do not rely on calculated and estimated stimulation values, which are too small in many cases and too large in others.

The conversion unit can be integrated into the magnetic resonance apparatus, particularly as a sub-program with driving electronics and evaluation electronics, with the measuring amplifier preferably being wirelessly connected to the MR apparatus.

DESCRIPTION OF THE DRAWING

The single FIGURE schematically illustrates an apparatus for increasing the efficiency of the gradient system of a magnetic resonance apparatus constructed and operating in accordance with the invention.

DESCRIPTION OF THE PREFERRED EMBODIMENTS

The inventive PNS sensor 1 can be attached to an arbitrary location at the body, such as by an easily releasable adhesive such as to the underarm in the exemplary embodiment. The PNS sensor is composed of a test coil 3 and a measuring electrode 4 arranged in its center, which are both attached to or below a foil or film 5, which is attached to the body. The test coil 3 and the measuring electrode 4 are connected to an adjustable measuring amplifier 6, which can be regulated in terms of frequency and which can generate pulse trains of various frequencies and amplitudes so that corresponding magnetic field pulses are applied to the body of the patient by the coil 3. The nerve reaction to the excitation pauses is detected by the measuring electrode 4. As soon as a peripheral nerve stimulation (PNS) occurs at the patient, the electrode 4 reacts and therefore signifies that the peak load limit of the patient is reached for a changing magnetic field of the applied size. The measuring amplifier 6—as indicated by the double arrow 7—is preferably wirelessly connected to the tomography apparatus 8. The apparatus 8 can execute a sub-program by means of driving electronics and evaluation electronics and, contains a conversion unit in order to carry out a scaling of the stimulation threshold of the patient in the MR tomography apparatus 8. On the basis of the current values, which have been applied to the test coil 3, and the magnetic fields arising therefrom, a projection onto the predetermined field calculations of the gradient coils that are stored in the MR apparatus can ensue, and an adjustment can be undertaken as a result thereof, so the gradient coils operate at a level just below the excitation limit of peripheral nerve stimulations of the respective patient.

The variable electrical field can be generated with a measuring coil instead of with an electro-stimulation device, but this has difficulty of correlation with the excitation by the magnetic fields of the gradient coils. Therefore, the nerve twitching alternatively can be determined by information from the patient or can be optically determined, for example by observing the twitching of the patient, instead of determining the initial nerve reaction by a measuring electrode. The measuring amplifier can be connected to the MR apparatus 8 by radio, infrared or by a fixed electrical connecting line as well.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for optimally utilizing the efficiency of a gradient system of a magnetic resonance tomography apparatus, comprising the steps of:

independent of said gradient system, individually determining a sensitivity of a patient with respect to peripheral nerve stimulation, prior to subjecting the patient to a magnetic resonance examination employing said gradient system, by applying a variable electrical field to the patient;

independent of said gradient system, identifying a response of the patient to the variable electrical field and determining, exclusively from said response, a corresponding maximum magnetic field, usable in the magnetic resonance examination of the patient, by scaling from the electric field; and adjusting said magnetic resonance apparatus to operate said gradient system no higher than said maximum magnetic field during the magnetic resonance examination of the patient.

2. A method as claimed in claim 1 comprising generating said variable electrical field by electro-stimulation of said patient with a test electrode attached to a body of the patient.

3. A method as claimed in claim 1 comprising generating said variable electrical field as an induction field with a test coil attached to the body of the patient.

4. A method as claimed in claim 3 comprising detecting said peripheral nerve stimulation, at a time after applying said variable electrical field, with a measuring electrode.

5. A method as claimed in claim 4 comprising disposing said measuring electrode in a center of said test coil.

6. A method as claimed in claim 4 comprising employing said test coil as said measuring electrode.

7. A method as claimed in claim 1 comprising detecting said peripheral nerve stimulation, at a time after applying said variable electrical field, with a measuring electrode.

8. A method as claimed in claim 1 comprising, in said magnetic resonance examination, generating a gradient field with said gradient system having a gradient field time function, and applying said variable electrical field with an electrical field time function corresponding to said gradient field time function.

9. In a magnetic resonance tomography apparatus having a gradient system, a device for optimally utilizing the efficiency of the gradient system, comprising:

a measuring amplifier which emits a variable electrical field to a test coil independent of said gradient system, said test coil being adapted for interaction with a patient prior to subjecting said patient to a magnetic resonance examination employing said gradient system, said variable electrical field producing a peripheral nerve stimulation in said patient;

a test electrode, independent of said gradient system, connected to said measuring amplifier adapted for measuring a characteristic of said electric field associated with said peripheral nerve stimulation exclusively of said patient;

a conversion unit for scaling said electric field associated with said peripheral nerve stimulation to a maximum gradient magnetic field producible by said gradient system; and a control unit in communication with said conversion unit for operating said gradient system during said magnetic resonance examination of said patient to produce gradient magnetic fields which do not exceed said maximum gradient magnetic field.

10. A device as claimed in claim 9 wherein said conversion unit comprises a memory containing a field calculation for each gradient orientation and each patient position and wherein said gradient unit correlates said gradient orientation and said patient position associated with said electric field when scaling said test field.

11. A device as claimed in claim 9 wherein said conversion unit is integrated into said magnetic resonance apparatus and wherein said measuring amplifier is in wireless communication with said control unit.

12. A device as claimed in claim 9 wherein said test electrode is disposed in a center of said test coil.

13. A device as claimed in claim 9 wherein said test electrode comprises said test coil.

* * * * *